United States Patent [19]

Murata et al.

[11] Patent Number: 5,263,370
[45] Date of Patent: Nov. 23, 1993

[54] LIQUIDOMETER

[75] Inventors: Michihiro Murata, Kyoto; Akira Kumada, Yokohama; Kenji Matsuo, Sagamihara; Shigeo Yamazaki, Yokohama, all of Japan

[73] Assignee: Murata Mfg. Co., Ltd., Kyoto, Japan

[21] Appl. No.: 692,726

[22] Filed: Apr. 29, 1991

[30] Foreign Application Priority Data

May 8, 1990 [JP] Japan .................. 2-118019

[51] Int. Cl.$^5$ .................................. G01F 3/00
[52] U.S. Cl. ........................... 73/226; 73/861; 73/304 R; 128/771
[58] Field of Search ............. 73/215, 223, 861, 304 R, 73/864.11, 864.51, 864.86; 128/760, 761, 771

[56] References Cited

U.S. PATENT DOCUMENTS

| | | |
|---|---|---|
| 3,919,455 | 11/1975 | Sigdell et al. .................. 73/861 |
| 4,169,377 | 10/1979 | Scheib ........................ 73/304 |
| 4,343,316 | 8/1982 | Jespersen . | 
| 4,346,596 | 8/1982 | Diamant et al. ................ 73/215 |
| 4,485,762 | 12/1984 | Sutton et al. . | 
| 4,589,280 | 5/1986 | Carter et al. ................. 128/760 |
| 4,758,409 | 7/1988 | Uffenheimer ................ 73/864.51 |
| 5,148,708 | 9/1992 | Murata et al. ................. 73/304 R |

Primary Examiner—Herbert Goldstein
Assistant Examiner—R. Biegel
Attorney, Agent, or Firm—Oliff & Berridge

[57] ABSTRACT

A liquidometer composed of a siphon for emitting a sample liquid stored in a reservoir and a liquid level sensor for sensing the level of the sample remained in the reservoir. The siphon further includes a pair of sensors for counting the number of emission thereof, while the liquid level sensor includes two rows of resistive film with a plurality of sensing elements embedded therein. Outside the liquidometer, there are provided a counter connected to the emission sensor, a level calculator connected to the liquid level sensor, and a calculator coupled to both. A gross amount of the sample liquid having been measured for a period of hours is obtained by adding together a count signal from the counter which represents the quantity of the sample liquid fully stored in the reservoir and a signal from the level counter which represents the liquid level of the remaining sample liquid. Moreover, variations in the quantity of the sample for a predetermined period is computed by the calculator in response to its internal clock.

10 Claims, 1 Drawing Sheet

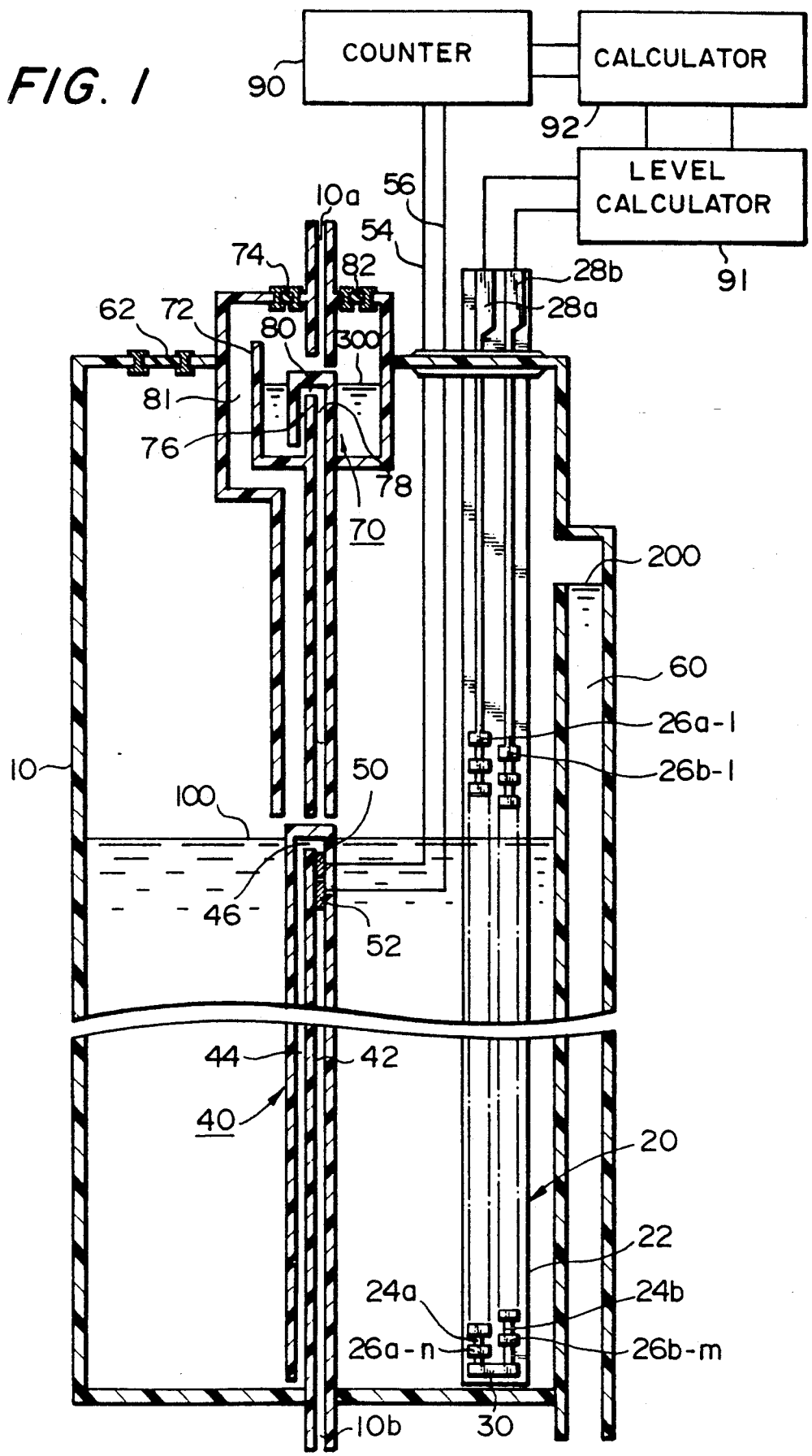

LIQUIDOMETER

BACKGROUND OF THE INVENTION

1. Field of the Invention

This invention relates to a liquidometer, and more particularly to an improved liquidometer for continuously measuring small quantities of a sample liquid by integrating flow data obtained from a series of measurements taken in a predetermined period.

2. Description of the Invention

In chemical processing or when measuring a body liquid of a patient in a hospital, it is necessary to successively measure the quantity of a sample liquid having a relatively small flow rate, that is a flow rate of less than 100 cc per minute, with high accuracy and resolution.

For instance, the amount of urine a patient under treatment discharges in a day provides information vital for a doctor to diagnose the condition of the patient accurately. Although such excretions occur in fairly small amounts in a unit period, the gross amount of them when integrated over a period of hours becomes quite large. Accordingly, there has arisen a need for a liquidometer which is capable of accurately effecting a successive recording of the liquid emissions.

Heretofore, a thermal type mass flow meter has been used for successively recording variations in the quantity of excretions with elapsed time. However, a major drawback of such existing apparatus is that the accuracy of the measurement becomes unstable due to changes in flow, or errors occur in the result because the mass or specific heat of the sample, which are used as parameters in the measurement method, can be altered by the presence of other components in the sample liquid.

Further, in the existing flow meter, since a thermal load is applied to the sample liquid, the sample is thermally impaired by a temperature change. Accordingly, such an existing flow meter is not suitable for measuring a chemically treated liquid or body liquid such as urine or the like.

SUMMARY OF THE INVENTION

This invention aims to overcome the drawbacks set forth in the above, and an object of the invention is to provide an improved liquidometer which is capable of continuously measuring the flow rate of a sample liquid having a small quantity, recording variations in the quantity of the sample during a predetermined period, and obtaining a gross amount of the sample liquid by integrating results of a series of measurements for a given hour.

To this aim, according to one aspect of the invention, there is provided a liquidometer comprising a reservoir for temporarily storing a sample liquid and a liquid level sensor, disposed inside of the reservoir, for measuring the level of the sample liquid, whereby it is possible to measure the quantity of the sample liquid having a small quantity with high accuracy.

Moreover, at the outlet of the vessel, an outlet-side siphon is provided. This siphon emits the stored sample whenever a given capacity of the reservoir is reached. The reservoir further comprises an emission sensor for sensing the number of emission of the outlet-side siphon, whereby it is possible to record the number of emissions conducted within a relatively long predetermined period.

Therefore, according to this invention, the sample liquid is emitted from the outlet-side siphon within a short period whenever a given capacity of the reservoir is reached, so variations in the quantity of the sample liquid are measured by the liquid level sensor with high accuracy.

Thus, a measurement with high resolution and accuracy is effected in the reservoir having a small capacity. Accordingly, an accurate measurement is repeatedly effected at every emission of the outlet-side siphon. Moreover, partly because the accurate measurement is continuously effected every time the outlet-side siphon emits the stored sample and partly because the number of emissions is counted by a clock of the counter 90, it is possible to measure a gross flow rate of the sample liquid and record variations in the quantity of the sample liquid within a predetermined period.

BRIEF DESCRIPTION OF THE DRAWINGS

The novel features believed characteristic of the invention are set forth in the appended claims. The invention itself, however, as well as other features and advantages thereof will be best understood by reference to the detailed description which follows read in conjunction with the accompanying drawings, wherein;

FIG. 1 is a cross-sectional plan view showing a liquidometer according to an embodiment of the present invention used in measuring a quantity of urine.

DETAILED DESCRIPTION OF THE PREFERRED EMBODIMENTS

Referring to the accompanying drawing, a preferred embodiment of the present invention will be described hereunder.

FIG. 1 is a cross-sectional view showing a liquidometer embodying the present invention. In the embodiment, the liquidometer is illustrated as an apparatus for measuring variations with time in the quantity of excreted urine of a patient in a hospital.

A reservoir 10 is a hermetically sealed container made from plastic or stainless steel. In this embodiment, for visual observation of the color and turbidity of the urine held inside the reservoir, at least one side of the reservoir 10 has a transparent wall.

The reservoir 10 includes an inlet 10a and an outlet 10b. By way of a non-illustrated tube from the patient, urine is introduced into the inlet 10a, whereas the urine is emitted from the outlet 10b to be led to another non-illustrated reservoir.

Inside the reservoir 10, there is provided a liquid level sensor 20 being formed of a sensor whose resistance varies depending on the conducting state of electrode disposed along the length of a resistive film.

As such liquid level sensor is proposed in the applicant's copending U.S. patent applications Ser. No. 537,174 entitled "Device for measuring displacement" and Ser. No. 626,616 entitled "Body fluid excretion measurement apparatus for medical application".

In more detailed description of the liquid level sensor, two columns of resistive film are screen-printed or evaporated on an insulating substrate 22 which is adhered to the inner wall of the reservoir 10 in a depth direction parallel to each other.

Electrodes $26a$-1 through $26a$-n in column "a" of a liquid level sensor are disposed offset with respect to the position of electrodes $26b$ through $26b$-m in column "b" of the level sensor.

Top end electrodes 26a-1 and 26b-1 are integrally formed with lead terminals 28a and 28b which are positioned outside the reservoir 10, and electrically coupled with a liquid level calculator 91.

Bottom end electrodes of the 26a and 26b are electrically connected to each other by means of a common electrode 30.

Staggered arrangement of both liquid level sensor columns 26a and 26b results in establishing an electrical connection between the electrodes 26a and 26b because of the electrical conduction between the resistive films 24a and 24b by means of the sample liquid in the reservoir 10. In the case of a sample liquid containing electrolytic material, urine for example, it is possible to detect the level of the sample liquid as an electrical signal by the use of variations in a resistance value. The signal from the lead terminals 28a and 28b is then input to the liquid level calculator 91, and output as the quantity of the sample liquid. In the drawing, the interval between the electrodes 26a and 26b is shown relatively wide for facilitating the explanation. By reducing this interval, a measurement with high resolution and accuracy can be achieved. In the case of a reservoir having a capacity of 200 cc, it is possible to obtain a resolution capacity of 1 cc with ease.

This invention is characterized in that an outlet-side siphon 40 is provided at the outlet 10b of the reservoir 10. The siphon 40 includes an outlet-side channel 42 joining the outlet 10b and an inlet-side channel 44 which has an opening at the bottom of the reservoir 10, and both of the channels are linked together at the crest of the channel 46.

With this structure, when the sample fluid is stored up to the level 100, the sample fluid flows over the crest of the inlet-side channel 44 and drains into the outlet-side channel 42. The moment the sample fluid exceeds the level 100, the outlet-side siphon 40 entails downward flow of the sample fluid stored in the reservoir 10 out from the outlet 10b, thereby emitting the reserved sample fluid within a considerably short period.

In this embodiment, the reservoir 10 has a constant reservoir capacity of the level 100 which determines the capacity of 200 cc.

According to this embodiment, until the sample liquid is stored up to the capacity of 200 cc inside the reservoir 10, the level of the liquid is successively measured by the liquid level sensor 20 with high accuracy. When the reservoir 10 is filled with the sample liquid to full capacity, i.e. 200 cc, this stored liquid is then emitted from the outlet 10b by siphonage within a significantly short period.

Upon completion of this emission, the next cycle of the inflow of the sample starts, whereby it is possible to constantly measure the sample liquid by the liquid level sensor 20 with high accuracy inside the reservoir 10.

The number of emissions from the outlet-side siphon 40 are counted by an outlet-side sensor composed of electrodes 50 and 52 provided in the outlet-side channel 42.

Specifically, since urine as being a sample liquid in this embodiment is electrolyte, the electrodes 50 and 52 enter conductive state when the sample liquid drains into the outlet-side channel 42 of the siphon 40 once having been stored in the reservoir 10 up to the constant capacity. This conductive state can be detected and output as an emission count signal from the terminals 54 and 56 to a counter 90.

The count signal from the counter 90 is then multiplied by the capacity of the reservoir 10 in response to an internal clock of a calculator 92. The calculator 92 also adds this multiplied data to liquid level data obtained by the level calculator 91 to produce a gross amount of the sample liquid.

Thus, every time the sample liquid is stored up to a predetermined capacity, the measurement is updated, whereby it becomes possible to measure variations in the quantity of the sample liquid with elapse of time. According to this invention, even when the gross amount of the sample liquid is drastically changed, an accurate measurement can be surely effected by means of the reservoir having a constant capacity.

In this embodiment, since an overflow channel 60 is provided inside the reservoir 10, if the reservoir 10 is filled with the sample liquid up to an overflow level designated by the numeral 200, the sample liquid is forcibly emitted outside through the overflow channel 60.

Under normal operation, the sample liquid is never stored up to the level 200 inside the reservoir 10. However, even if the siphon 40 clogs due to some unexpected cause, the sample liquid for example, urine, can be forcibly emitted from the reservoir.

Moreover, a dust filter 62 for ventilation is provided on the top of the reservoir 10 so that an atmospheric pressure can be introduced into the reservoir with the reservoir hermetically sealed.

Further, the reservoir 10 has a pre-reservoir 72 including an inlet-side siphon 70 provided at the bottom end of the inlet 10a which operates similarly to the outlet-side siphon 40 set forth in the above. This pre-reservoir 72 is useful to temporarily store a newest sample. From this reservoir, it is possible to obtain the most recently discharged urine. To withdraw this sample liquid from the pre-reservoir 72, a rubber filter 74 is removably provided on the top surface of the pre-reservoir 72.

The inlet-side siphon 70 is composed of an inlet-side channel 76 and an outlet-side channel 78, and both channels are joined together at a crest portion thereof designated by the reference numeral 80. With such a structure, when the sample liquid exceeds the level 300, the liquid drains from the pre-reservoir 72 into the reservoir 10 through the inlet-side siphon 70.

In the case of the urine measuring apparatus described in this embodiment, a pre-reservoir capacity is set to about 6 cc, and newly sampled urine is, therefore, temporarily stored therein with the capacity of 6 cc constantly.

The pre-reservoir 72 and the reservoir 10 are linked together by means of an overflow channel 81, and accordingly the sample liquid can be introduced into the reservoir 10 even when the inlet-side siphon 70 malfunctions due to clogging.

In the drawing, a dust filter 82 for ventilation is disposed on the top surface of the sample reservoir 72, and an atmospheric pressure is introduced into the pre-reservoir 72 through this filter.

The operation of the liquidometer, according to this invention, having the above-described structure will now be described.

A sample liquid to be measured, urine excreted from a patient in this embodiment, is intermittently introduced through the inlet 10a and temporarily stored in the pre-reservoir 72.

Accordingly, the newest sample can be withdrawn from the sample reservoir 72 through the rubber filter 74 by means of a non-illustrated syringe. It is also possible to ensure that the sample liquid to be introduced into the reservoir 10 is always introduced in consistent units of volume.

When the sample liquid exceeds the level 300, all of the sample liquid is introduced into the reservoir 10 by operation of the siphon 70. Variations in the quantity of this sample liquid are then accurately measured by a liquid level sensor 20.

The storing and emitting of the sample liquid is repeated, and when the liquid level reaches the level 100 in the reservoir 10, the sample liquid of a predetermined capacity stored in the reservoir 10 drains into the outlet-side siphon 40. With repetition of such operation, variations in the quantity of the sample for a predetermined period are recorded.

Thus, according to this invention, since the sample liquid having a relatively small quantity is accurately and continuously measured with a predetermined capacity of the reservoir 10, it is possible to precisely measure variations in the quantity of the sample liquid with high resolution, and also it is possible to obtain the number of emission cycles given from the result from the emission sensor with ease.

Although the existing liquidometer which measures the level of the sample by storing all of the sample in the reservoir only provides a result with an accuracy of about 5%, the liquidometer embodying the present invention can provide a result with an accuracy of about 0.1%.

In the embodiment set forth, though the emission sensor is positioned at the inside of the outlet-side siphon 40, it goes without saying that the emission sensor can be incorporated into the liquid level sensor 20. Moreover, in addition to the resistive type sensor shown in the drawing, ultrasonic waves or other liquid level sensing devices can be employed for use in the liquid level sensor.

As has been described, according to this invention, the sample liquid having a small quantity can be continuously measured for hours, and thereby variations in the quantity with time can be recorded with high accuracy.

While this invention has been described with reference to an illustrative embodiment, this description is not intended to be construed in a limiting sense. Various modifications of the illustrative embodiment, as well as other embodiments of the invention, will be apparent to those who are versed in the art upon reference to this description. It is, therefore, contemplated that the appended claims will cover any such modifications or embodiments as fall within the true scope of the invention.

What is claimed is:

1. A liquidometer for measuring the quantity of a sample liquid, comprising:
   (a) a main container for holding the sample liquid and having a predetermined capacity;
   (b) a means for sensing a level of sample liquid held in the main container, wherein the level sensing means comprises a plurality of columns of resistive films with sensing elements, and the sensing elements in one resistive film column are arranged offset with respect to the sensing elements on a next-adjacent column;
   (c) a means coupled to the sensing means and for calculating the quantity of the sample liquid stored in the main container on the basis of an output from the sensing means;
   (d) a siphon means for emitting the sample liquid stored in the main container using atmospheric pressure when the sample has reached a predetermined level;
   (e) a means, disposed inside the siphon means, for sensing the emission of the sample liquid;
   (f) a means connected to the emission sensing means for counting the number of signals output from the emission sensing means; and
   (g) a means, coupled to the calculating means and the counting means, for adding together the output from the calculating means and the output from the counting means.

2. A liquidometer according to claim 1, wherein said plurality of columns of resistive film are arranged parallel to each other.

3. A liquidometer for measuring the quantity of a sample liquid, comprising:
   (a) a main container for holding the sample liquid and having a predetermined capacity;
   (b) a means for sensing a level of sample liquid held in the main container, wherein a sample storing chamber located in the upper portion thereof for temporarily storing the sample before introduction into the main container and having therein a sub container for storing the sample liquid poured from an inlet, a filter for sampling the sample liquid by means of a syringe, and an emitting means for emitting the sample liquid a predetermined level
   (c) a means coupled to the sensing means for calculating the quantity of the sample liquid stored in the main container on the basis of an output from the sensing means;
   (d) a siphon means for emitting the sample liquid stored in the main container using atmospheric pressure when the sample has reached a predetermined level;
   (e) a means, disposed inside the siphon means, for sensing the emission of the sample liquid;
   (f) a means connected to the emission sensing means for counting the number of signals output from the sensing means; and
   (g) a means, coupled to the calculating means and the counting means, for adding together the output from the calculating means and the output from the counting means.

4. A liquidometer according to claim 3, wherein the sample liquid emitting means is a siphon.

5. A liquidometer according to claim 3, wherein the liquidometer further includes therein an overflow channel positioned between an uppermost end of the siphon means in the main container and an uppermost end of the siphon means in the sub container.

6. A liquidometer according to claim 4, wherein the siphon in the sub container includes therein an overflow channel whose inlet is positioned over an uppermost end of the siphon in the sub container.

7. A liquidometer according to claim 6, wherein the main container comprises a dust filter for ventilation on the top thereof.

8. A liquidometer according to claim 1, wherein the siphon means comprises an inlet-side channel and an outlet-side channel, and the emission sensing means is provided in the outlet-side channel.

9. A liquidometer for measuring the quantity of a sample liquid, comprising:

(a) a main container for holding the sample liquid and having a predetermined capacity;

(b) a means for sensing a level of sample liquid held in the main container, wherein the level sensing means comprises a plurality of columns of resistive films with sensing elements, and the sensing elements in one resistive film column are arranged offset with respect to the sensing elements on a next-adjacent column;

(c) a siphon means for emitting the sample liquid stored in the main container using atmospheric pressure when the sample has reached a predetermined level;

(d) a means, disposed inside the siphon means, for sensing the emission of the sample liquid; and (e) a means for measuring the output of a sample liquid.

10. A liquidometer according to claim 6, wherein the level sensing means detects the change in volume by a change in resistance value of the resistive film.

* * * * *